United States Patent [19]

Constantino

[11] Patent Number: 4,836,392
[45] Date of Patent: Jun. 6, 1989

[54] UPRIGHT BABY-NIPPLE SANITIZER

[76] Inventor: Cynthia L. Constantino, P.O. Box 10464, Torrance, Calif. 90505

[21] Appl. No.: 289,811

[22] Filed: Dec. 23, 1988

[51] Int. Cl.$^4$ .............................................. B65D 6/08
[52] U.S. Cl. .................................... 211/181; 220/19; 294/158
[58] Field of Search ................... 211/181, 41; 220/19; 294/158

[56] References Cited

U.S. PATENT DOCUMENTS

| | | | |
|---|---|---|---|
| 2,732,096 | 1/1956 | Siciliano | 220/19 X |
| 2,896,815 | 7/1959 | Longan | 220/19 X |
| 3,050,073 | 8/1962 | McMillan | 220/19 X |
| 3,778,002 | 12/1973 | Alleweireldt | 294/158 X |
| 4,498,594 | 2/1985 | Elder | 211/41 X |
| 4,512,489 | 4/1985 | Green et al. | 220/19 |
| 4,732,291 | 3/1988 | McConnell | 220/19 |
| 4,748,993 | 6/1988 | Llewellyn | 211/181 X |

Primary Examiner—Robert W. Gibson, Jr.
Attorney, Agent, or Firm—Monty Koslover

[57] ABSTRACT

A baby-nipple sanitizer for use in a dishwasher, the device sized and arranged to hold four or five nipples upright on prongs in a basket, while a lid prevents the nipples from being toppled by action of the hot water, and filling with stale water. Provision is also made for stringing body bottle collars on the handle, which can be loosened from the basket at one end for this purpose. The sanitizer is small in size and may be secured conveniently in any position on dishwasher racks.

2 Claims, 1 Drawing Sheet

UPRIGHT BABY-NIPPLE SANITIZER

BACKGROUND OF THE INVENTION

Parents of infants need to wash their baby bottles daily and, at the same time, sanitize the bottle nipples and their collars. The inventor, a young mother, found this to be inconvenient and time-consuming using today's sanitizers. There are a number of sanitizers available. Many sanitizers are intended for heating on a kitchen range. The bottles, nipples and collars are placed inside a container having a water compartment. Steam generated by heating, cleanses the components in the sanitizer.

Frequently, stale water and particles are trapped in the nipples which have been turned upside down by the action of the water. This makes it necessary to repeat the cleansing process.

Some sensitizers are intended for use in a dishwasher. Such sanitizers have advantages in that no separate equipment standing on a range is needed, and the drying cycle of the dishwasher will dry the nipples and collars, eliminating hand drying. However, these 'basket' type sanitizers have drawbacks, reducing their utility. In use, the nipples and collars are placed loosely in the basket. When the washing and drying cycles have finished, some nipples will have turned on a side or upside down, allowing stale water and particles to be trapped in the nipples. Sanitization will therefore be ineffective and unsatisfactory. Furthermore, a review of available 'basket' type sanitizers shows that typically they are large and awkward fitting on either rack of dishwashers. In the inventor's experience, it is seldom necessary to sanitize more than four or five bottles and nipples a day for a baby. Therefore, a small basket holding four or five nipples and collars should be adequate. From the foregoing, it is clear there exists a need for a baby nipple sanitizer that will keep the nipples upright during cleansing, and can be stacked on any dishwasher rack.

SUMMARY OF THE INVENTION

The invention comprises a cylindrical shaped, coated-wire basket, having a hinged lid and an attached curved wire handle. Five vertical prongs attached to the bottom of the basket are used each to hold a baby-nipple upright. The hinged lid, when closed, prevents the nipples from being lifted off the prongs and turned upside down. The curved wire handle opens at one end, allowing nipple collars to be strung on the handle for washing. The sanitizer is small, being typically approximately 4½ inches in diameter, allowing it to be secured anywhere on a dishwasher rack; and constructed to allow the dishwasher rack prongs to go through it, holding the sanitizer in place.

Accordingly, it is a principal object of this invention to provide a baby-nipple sanitizer that will keep the nipples upright during cleansing, and is intended for use in dishwashers.

Another object is to provide a baby-nipple sanitizer that can be secured easily anywhere on a dishwasher rack.

Further objects and advantages of this invention may become apparent from the study of the following specification, the claims and the attached drawings.

DESCRIPTION OF THE PREFERRED EMBODIMENT

Figure 1:
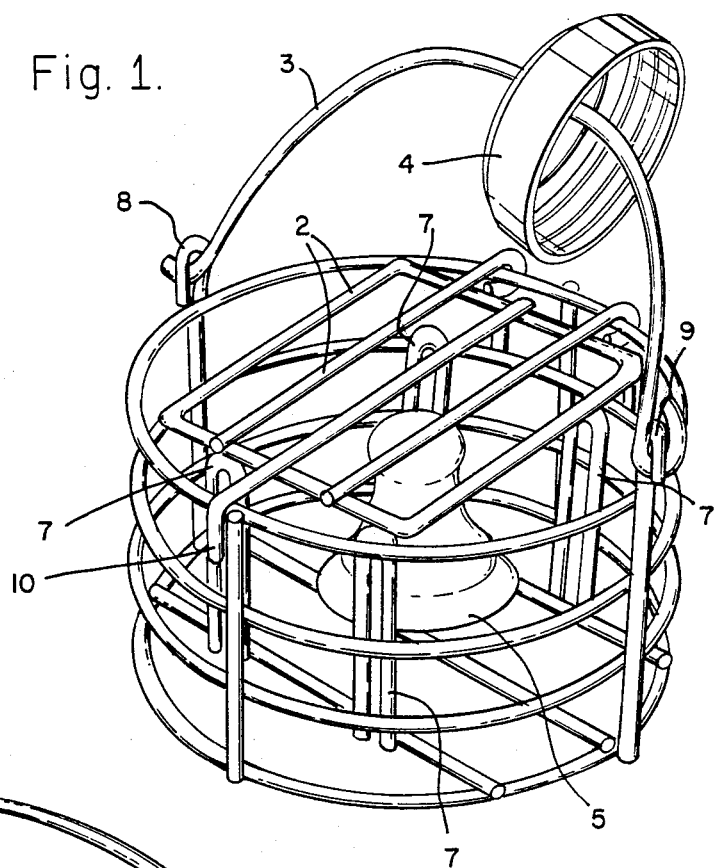
FIG. 1 is a perspective view of the present invention, showing one baby-nipple and collar in place, ready for placing in the dishwasher.

Referring particular to the drawings, there is shown in FIG. 1 a preferred embodiment of the upright baby-nipple sanitizer. In this view, only one nipple 5 and one collar 4 are shown in place, although the device provides mounting prongs 7 for five nipples and five or more collars on the handle 3. The device is shown as it would be, when ready for placing in a dishwasher rack, with the lid 2 closed and the handle 3 in position. As can be seen, there is room between the bottom cross-ribs for one or two dishwasher rack prongs to be inserted as necessary for securing to the rack.

Figure 2:
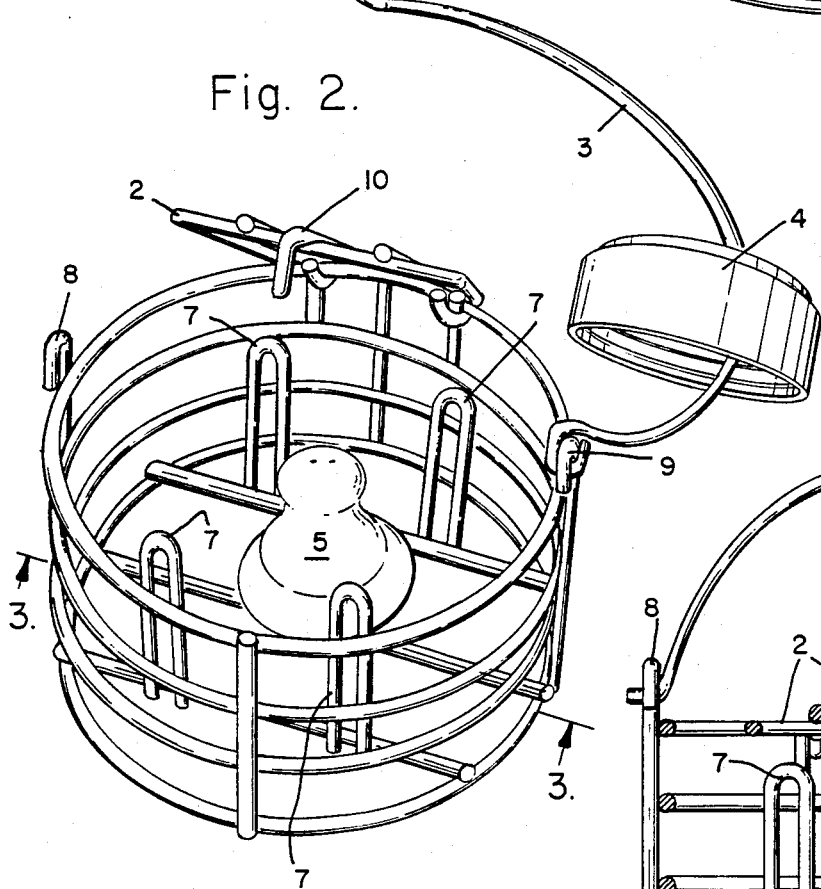
FIG. 2 is a perspective view of the present invention, showing the hinged lid open for loading and the handle released from its holding hook at one end, allowing collars to be strung on the handle.
Figure 3:
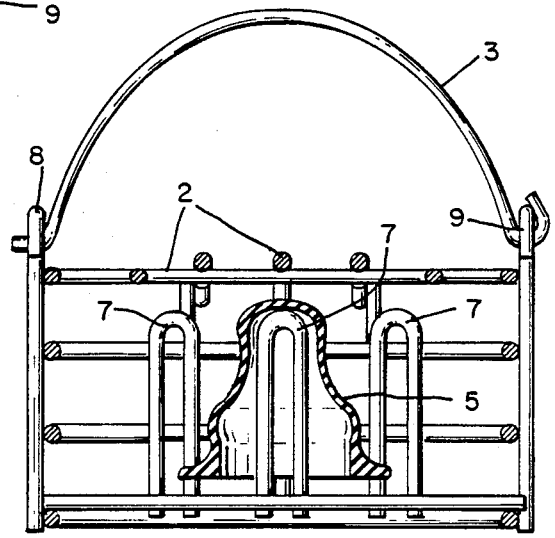
FIG. 3 is a front, sectional view of the device taken along line 3—3 of FIG. 2, showing the handle ends secured and the lid down in place.

Referring now also to FIGS. 2 and 3, it is shown that the device is made wholly of wire, bent and shaped as required. The device essentially comprises three assemblies or parts. These are the hinged wire lid 2, the handle 3 and the cylindrical basket. The wire is approximately 0.10 inch diameter thick, coated with a rubberized material suitable for withstanding dishwater heating temperatures. The hinged lid 2 is rectangularly shaped, 3 in. long by 2¼ in. wide made with four pieces of wire; with two hooked portions of wire at one longitudinal end serving as a hinge, and another hooked wire portion 10 at its distal longitudinal end serving as a closure hook. The wires are soldered or welded together in parallel to form the hinged lid 2.

Closure of the lid 2 is effected by pushing a hooked portion 10 of the lid 2 over the top wire of the basket. The rectangular shaped lid 2 is dimensioned with respect to the diameter of the cylindrical wire basket so that its hooked portion 10 fits tightly over the wire basket. When the lid 2 is closed, there is approximately one quarter inch space between the mounted nipples 5 and the lid 2, allowing the nipples movement upward of one quarter inch, but otherwise holding them vertically in place.

The curved wire handle 3 has one end shaped in a partly closed hook for fastening securely to the basket structure, and the other end open straight. The closed hook end is fastened to a first hooked portion 9 at the top of and on one side of the basket structure, and the open end of the handle 3 is slipped under the second hooked portion 8 diametrically across from the first. Since the wire handle 3 is slightly flexible, it can easily have its open end inserted in place or removed as desired.

The basket portion of the device is approximately 4½ inches in diameter by 2½ inches high. Four circular pieces of wire, 4½ inches in diameter are welded to four vertical pieces of wire, arranged equidistantly around the circumference, forming a cylinder open at the top end 4½ inches in diameter by 2¼ inches high. Two of the vertical pieces of wire have hooked portions 8 and 9, that protrude above the top rim of the basket and serve as fasteners for the handle 3. Three pieces of straight rigid wire are equally spaced across the bottom of the basket and welded at both ends to the bottom ring of the basket. Five prongs 7 made of wire, shaped in a 'hairpin' or tight 'U' shape are located and spaced approximately 1¼ inch to 1½ inches apart in the bottom of the basket and welded to the bottom cross pieces, so that the prongs 7 are vertical and have their curved ends facing upwards.

The lid 2 is finally fastened to the basket by bending its two paralleled hooked portions, serving as the hinge, over the top wire of the basket and pinching the hooked portions closed. In this manner, there is a sufficient wire radius to permit easy hinge action.

FIG. 3, which is a cross-sectional view, shows the typical spacing and arrangement of the wires forming the basket, the lid 2 and the handle 3. The cross-sectional view of a typical nipple in place on a prong 7, shows the degree of restraint of movement. In the dishwasher washing and drying cycles, the hot water and the hot air can easily penetrate all the inner and outer surfaces of the nipples, assuring proper cleansing and removal of adhered particles. No stale water can remain trapped inside the vertically mounted nipples.

Having described the invention, what is claimed is:

1. A baby-nipple sanitizer device comprising: a cylindrical wire basket, a wire lid and a wire handle; said cylindrical wire basket being formed from approximately 0.10 inch diameter wire, coated with a rubberized material suitable for dishwasher heating temperatures, said wire basket having a cylindrical shape, open at its top end, and measuring approximately 4½ inches in diameter by 2¼ inches high, said wire basket having a multiplicity of wire prongs, soldered or welded to the bottom rungs of said wire basket, and arranged vertically and equally spaced apart to accommodate baby nipples, one on each wire prong, said wire basket having two hooked portions of wire 180 degrees apart, attached protruding above the top rim of said basket and serving as hook fastenings for said wire handle; said wire lid being hingedly connected to said wire basket by two hooked portions that extend from one longitudinal end and serve a hinge, said wire lid having a third hooked portion extending at the distal end from the hinge and serving to hold said lid closed when said third hooked portion is pushed over the top wire of said wire basket, said wire lid being formed from approximately 0.10 inch diameter wire, coated with a rubberized material suitable for dishwasher heating temperatures, said wire lid being rectangularly shaped, approximately 3 inches ling by 2¼ inches wide and sized to fit the diameter of said basket so that said lid will close tightly when pushed in place; said handle being made of a single piece of the same wire used for said basket contruction, said handle being curved in an arc approximately 2¼ inches in radius, and having one end shaped in a partly closed hook for fastening securely to one of the basket structure hooked portions, and the other end open straight for insertion in the opposing backet hooked portion; said wire basket prongs being sized and shaped to hold baby nipples upright so that when said lid is closed there is only approximately one quarter inch space between the top of the nipples and the lid, permitting nipple movement for cleansing but preventing them from toppling and filling with water; said wire basket having sufficient space between its bottom rungs, allowing the dishwasher rack prongs to be inserted for securing the device to the rack; said baby-nipple sanitizer being shaped and sized to allow its placing in any convenient position on the dishwasher rack.

2. The baby-nipple sanitizer device of claim 1 wherein:
   said wire handle is assembled to the wire basket with one end of the handle permanently secured and the other end able to be spring loose so that the collars from baby bottles may be strong on said wire handle for washing with the nipples.

* * * * *